(12) United States Patent
Hanson

(10) Patent No.: US 11,857,345 B2
(45) Date of Patent: Jan. 2, 2024

(54) PRESSURE SENSING GUIDEWIRES

(71) Applicant: BOSTON SCIENTIFIC SCIMED, INC., Maple Grove, MN (US)

(72) Inventor: Brian J. Hanson, Shoreview, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 449 days.

(21) Appl. No.: 15/254,678

(22) Filed: Sep. 1, 2016

(65) Prior Publication Data
US 2017/0065225 A1 Mar. 9, 2017

Related U.S. Application Data

(60) Provisional application No. 62/214,703, filed on Sep. 4, 2015.

(51) Int. Cl.
*A61B 5/0215* (2006.01)
*A61B 5/00* (2006.01)

(52) U.S. Cl.
CPC ........ *A61B 5/6851* (2013.01); *A61B 5/02154* (2013.01); *A61B 2562/0233* (2013.01); *A61B 2562/0247* (2013.01)

(58) Field of Classification Search
CPC .. A61M 25/09; A61B 5/0215; A61B 5/02007; A61B 18/082; A61B 2562/0247
See application file for complete search history.

(56) References Cited

U.S. PATENT DOCUMENTS

| 4,924,870 | A | * | 5/1990 | Wlodarczyk | ...... A61B 5/02154 600/480 |
| 5,106,455 | A | | 4/1992 | Jacobsen et al. | |
| 5,238,004 | A | | 8/1993 | Sahatjian et al. | |

(Continued)

FOREIGN PATENT DOCUMENTS

| CN | 201763322 U | 3/2011 |
| CN | 102908133 A | 2/2013 |

(Continued)

OTHER PUBLICATIONS

Liao, C.R., et al. "Optical fiber Fabry-Perot interferometer cavity fabricated by femtosecond laser micromachining and fusion splicing for refractive index sensing", Optics Express, 20(20):22813-22818, Sep. 24, 2012.

(Continued)

*Primary Examiner* — Nathan J Jenness
*Assistant Examiner* — Michael A Catina
(74) *Attorney, Agent, or Firm* — Seager, Tufte & Wickhem, LLP

(57) ABSTRACT

Medical devices and methods for making and using medical devices are disclosed. An example medical device may include a medical device for measuring blood pressure. The medical device may include an elongated shaft having a proximal region and a distal region and a lumen extending therethrough and an optical pressure sensing block disposed within the lumen, the optical pressure sensing block including a distal portion bearing a pressure sensing membrane and a proximal portion forming an optical fiber connector extending proximally from the proximal portion. The optical fiber connector may be configured to be coupled to an optical fiber extending through the lumen.

18 Claims, 11 Drawing Sheets

(56) References Cited

U.S. PATENT DOCUMENTS

| | | | |
|---|---|---|---|
| 5,392,117 | A | 2/1995 | Belleville et al. |
| 5,772,609 | A | 6/1998 | Nguyen et al. |
| 6,139,510 | A | 10/2000 | Palermo |
| 6,508,803 | B1 | 1/2003 | Horikawa et al. |
| 6,579,246 | B2 | 6/2003 | Jacobsen et al. |
| 6,766,720 | B1 | 7/2004 | Jacobsen et al. |
| 7,689,071 | B2* | 3/2010 | Belleville ............... G01L 19/04 385/13 |
| 8,557,129 | B2 | 10/2013 | Donlagic et al. |
| 8,655,117 | B2 | 2/2014 | Donlagic et al. |
| 2002/0072679 | A1 | 6/2002 | Schock et al. |
| 2003/0069522 | A1 | 4/2003 | Jacobsen et al. |
| 2004/0181174 | A2 | 9/2004 | Davis et al. |
| 2006/0209413 | A1* | 9/2006 | Kim ......................... G01J 3/26 359/577 |
| 2014/0081244 | A1* | 3/2014 | Voeller .................. A61M 25/01 604/528 |
| 2014/0363118 | A1 | 12/2014 | Wang et al. |
| 2015/0032011 | A1 | 1/2015 | McGowan et al. |
| 2015/0223707 | A1 | 8/2015 | Ludoph |

FOREIGN PATENT DOCUMENTS

| | | |
|---|---|---|
| JP | H0743222 A | 2/1995 |
| JP | 2015501184 A | 1/2015 |
| WO | 2013061280 A1 | 5/2013 |

OTHER PUBLICATIONS

Pinet, Eric, et al., "Ultra-miniature all-glass Fabry-Perot pressure sensor manufactured at the tip of a multimode optical fiber", Proc of SPIE, vol. 6770, pp. 67700U-1 to 67700U-8, 2007.

Chinese Family Member 201680064725.4 Reexamiation Reporting Letter, including summary, dated Mar. 29, 2023 with related Chinese literature.

\* cited by examiner

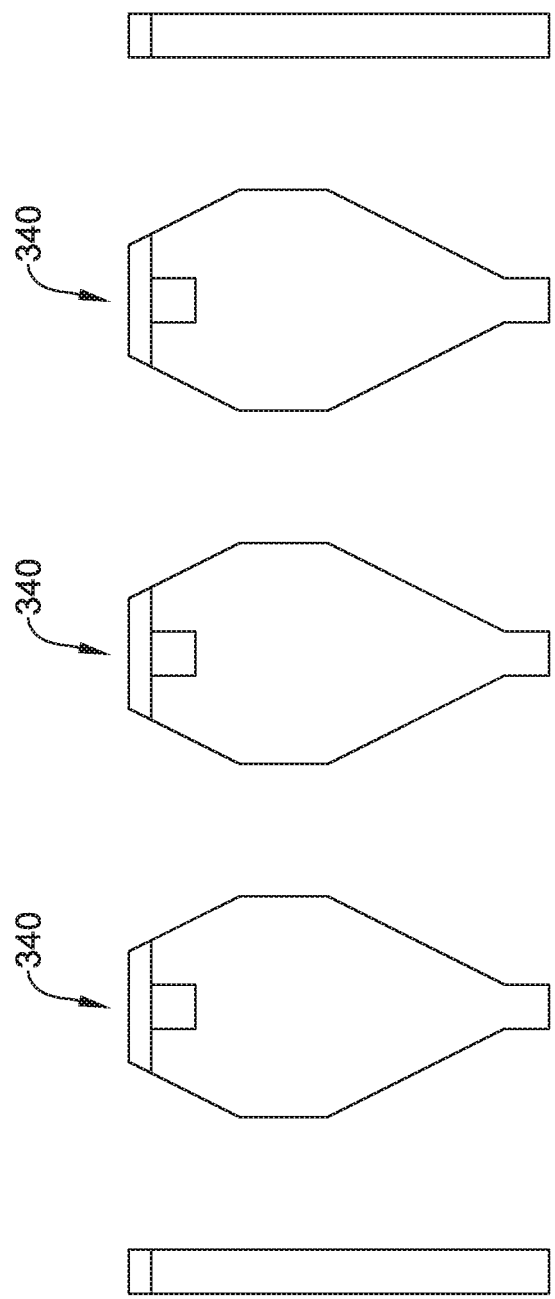

PRESSURE SENSING GUIDEWIRES

CROSS-REFERENCE TO RELATED APPLICATIONS

This application claims the benefit of priority under 35 U.S.C. § 119 to U.S. Provisional Application No. 62/214,703, filed Sep. 4, 2015, the entirety of which is incorporated herein by reference.

TECHNICAL FIELD

The present disclosure pertains to medical devices, and methods for manufacturing medical devices. More particularly, the present disclosure pertains to blood pressure sensing guidewires and methods for using pressure sensing guidewires.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device for measuring blood pressure is disclosed. The medical device for measuring blood pressure comprises:
  an elongated shaft having a proximal region and a distal region and a lumen extending therethrough;
  an optical pressure sensing block disposed within the lumen, the optical pressure sensing block including a distal portion and a proximal portion;
  a pressure sensing membrane disposed on the distal portion of the optical pressure sensing block;
  the proximal portion forming an optical fiber connector extending proximally from the proximal portion, the optical fiber connector configured to be coupled to an optical fiber; and
  an optical fiber extending through the lumen and coupled to the optical fiber connector.

Alternatively or additionally to any of the embodiments shown above, the optical fiber connector has a circular cross-sectional shape and has a diameter that is about the same as a diameter of the optical fiber.

Alternatively or additionally to any of the embodiments shown above, the optical fiber is fusion spliced to the optical fiber connector.

Alternatively or additionally to any of the embodiments shown above, the lumen includes an enlarged inner diameter portion within the distal region of the shaft, and the optical pressure sensing block is disposed within the enlarged inner diameter portion.

Alternatively or additionally to any of the embodiments shown above, the optical pressure sensing block further comprises a center portion configured to space the sensing membrane away from the lumen.

Alternatively or additionally to any of the embodiments shown above, the sensing membrane is eutectically bonded to the optical pressure sensing block.

Alternatively or additionally to any of the embodiments shown above, the elongated shaft comprises a tubular member having one or more slots formed therein.

Alternatively or additionally to any of the embodiments shown above, the medical device further comprises a tip member extending distally from the elongated shaft.

Alternatively or additionally to any of the embodiments shown above, the tip member comprises a shaping member and/or a coil member.

A pressure sensing guidewire is disclosed. The pressure sensing guidewire comprises:
  an elongated tubular member having a proximal region and a distal region and a lumen extending therethrough;
  an optical pressure sensing block disposed within the lumen, the optical pressure sensing block including a distal portion and a proximal portion;
  a pressure sensing membrane disposed on the distal portion of the optical pressure sensing block;
  the proximal portion forming an optical fiber connector configured to be coupled to an optical fiber; and
  an optical fiber extending through the lumen and including a distal end, the distal end coupled to the optical fiber connector.

Alternatively or additionally to any of the embodiments shown above, the optical fiber connector extends proximally from the proximal portion of the optical pressure sensing block and is configured to be fusion spliced to the distal end of the optical fiber.

Alternatively or additionally to any of the embodiments shown above, the optical fiber connector comprises a recess formed in the proximal portion of the optical pressure sensing block and configured to accommodate the distal end of the optical fiber therein.

Alternatively or additionally to any of the embodiments shown above, the lumen includes an enlarged inner diameter portion within the distal region of the elongated tubular member, and the optical pressure sensing block is disposed within the enlarged inner diameter portion.

Alternatively or additionally to any of the embodiments shown above, the optical pressure sensing block further comprises a central portion disposed between the distal portion and the proximal portion;
  the distal portion tapering from the central portion to a position proximate the pressure sensing membrane; and
  the proximal portion tapering from the central portion to the optical fiber connector;
  wherein the central portion spaces the sensing membrane away from the lumen.

Alternatively or additionally to any of the embodiments shown above, the pressure sensing guidewire further comprises a tip member extending distally from the elongated shaft.

Alternatively or additionally to any of the embodiments shown above, the tip member comprises a shaping member and/or a coil member.

A pressure sensing guidewire for measuring fractional flow reserve is disclosed. The pressure sensing guidewire for measuring fractional flow reserve comprises:
  an elongate shaft having a proximal region and a distal region and defining a lumen extending therethrough;
  wherein the distal region has a plurality of slots formed therein;
  an optical fiber extending within the shaft and including a distal end;

an optical pressure sensing block disposed within the lumen, the optical pressure sensing block including a distal portion, a proximal portion, and a center portion disposed between the distal portion and the proximal portion;

a pressure sensing membrane disposed on the distal portion of the optical pressure sensing block;

the proximal portion forming an optical fiber connector extending proximally from the proximal portion and fusion spliced to the distal end of the optical fiber;

the distal portion tapering from the center portion to a position proximate the pressure sensing membrane; and the proximal portion tapering from the center portion to the optical fiber connector.

Alternatively or additionally to any of the embodiments shown above, the optical pressure sensing block comprises glass.

Alternatively or additionally to any of the embodiments shown above, the pressure sensing guidewire further comprises a recess formed in the distal portion of the optical pressure sensing block beneath the pressure sensing membrane.

Alternatively or additionally to any of the embodiments shown above, the optical fiber connector is configured to improve the accuracy of a connection between the distal end of the optical fiber and the optical fiber connector.

A Fabry-Perot optical sensing device is disclosed. The Fabry-Perot optical sensing device comprises:

a sensor block including a proximal portion, a distal portion and an intermediate portion disposed between the proximal and distal portions, the intermediate portion having an outer diameter that is greater than an outer diameter of the distal portion and greater than an outer diameter of the proximal portion;

the distal portion defining a cavity therein; and a pressure sensing layer disposed over the cavity.

Alternatively or additionally to any of the embodiments shown above, the proximal portion has an optical fiber connector portion, and an optical fiber is connected to the optical fiber portion.

Alternatively or additionally to any of the embodiments shown above, the optical fiber connection portion has an outer diameter that is the same as an outer diameter of the optical fiber.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIGS. 8 through 11 show an illustrative but non-limiting manufacturing method.

Figure 1:
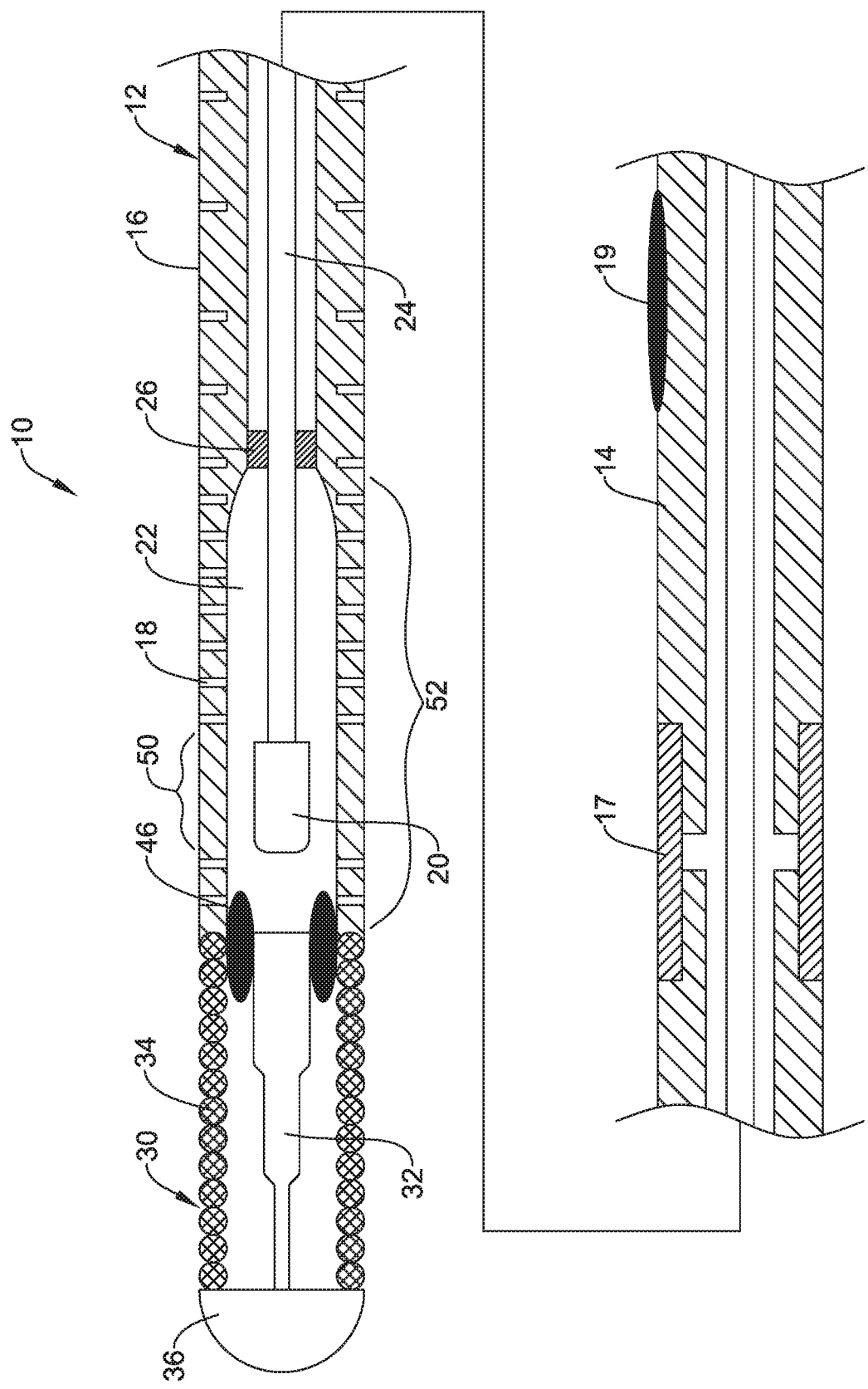
FIG. 1 is a partial cross-sectional side view of a portion of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

During some medical interventions, it may be desirable to measure and/or monitor the blood pressure within a blood vessel. For example, some medical devices may include pressure sensors that allow a clinician to monitor blood pressure. Such devices may be useful in determining fractional flow reserve (FFR), which may be understood as the pressure after a stenosis relative to the pressure before the stenosis (and/or the aortic pressure).

FIG. 1 illustrates a portion of an example medical device 10. In this example, medical device 10 is a blood pressure sensing guidewire 10. However, this is not intended to be limiting as other medical devices are contemplated including, for example, catheters, shafts, leads, wires, or the like. Guidewire 10 may include a tubular member or elongated shaft 12. Shaft 12 may include a proximal region 14 and a distal region 16. The materials for proximal region 14 and distal region 16 may vary and may include those materials disclosed herein. For example, distal region 16 may include a nickel-cobalt-chromium-molybdenum alloy (e.g., MP35-N). Proximal region 14 may include stainless steel. These are just examples. Other materials may also be utilized.

In some embodiments, proximal region 14 and distal region 16 are formed from the same monolith of material. In other words, proximal region 14 and distal region 16 are portions of the same tube defining shaft 12. In other embodiments, proximal region 14 and distal region 16 are separate tubular members that are joined together. For example, a section of the outer surface of regions 14/16 may be removed and a sleeve 17 may be disposed over the removed sections to join regions 14/16. Alternatively, sleeve 17 may be simply disposed over regions 14/16. Other bonds may also be used including welds, thermal bonds, adhesive bonds, or the like. If utilized, sleeve 17 used to join proximal region 14 with distal region 16 may include a material that desirably bonds with both proximal region 14 and distal region 16. For example, sleeve 17 may include a nickel-chromium-molybdenum alloy (e.g., INCONEL).

A plurality of slots 18 may be formed in shaft 12. In at least some embodiments, slots 18 are formed in distal region 16. In at least some embodiments, proximal region 14 lacks slots 18. However, proximal region 14 may include slots 18. Slots 18 may be desirable for a number of reasons. For example, slots 18 may provide a desirable level of flexibility to shaft 12 (e.g., along distal region 16) while also allowing suitable transmission of torque. Slots 18 may be arranged/distributed along distal region 16 in a suitable manner including any of those arrangements disclosed herein. For example, slots 18 may be arranged as opposing pairs of slots 18 that are distributed along the length of distal region 16. In some embodiments, adjacent pairs of slots 18 may have a substantially constant spacing relative to one another. Alternatively, the spacing between adjacent pairs may vary. For example, more distal portions of distal region 16 may have a decreased spacing (and/or increased slot density), which may provide increased flexibility. In other embodiments, more distal portions of distal region 16 may have an increased spacing (and/or decreased slot density). These are just examples. Other arrangements are contemplated.

A pressure sensor 20 may be disposed within shaft 12 (e.g., within a lumen 22 of shaft 12). While pressure sensor 20 is shown schematically in FIG. 1, it can be appreciated that the structural form and/or type of pressure sensor 20 may vary. For example, pressure sensor 20 may include a semiconductor (e.g., silicon wafer) pressure sensor, piezoelectric pressure sensor, a fiber optic or optical pressure sensor, a Fabry-Perot type pressure sensor, an ultrasound transducer and/or ultrasound pressure sensor, a magnetic pressure sensor, a solid-state pressure sensor, or the like, or any other suitable pressure sensor. In some cases, the sensor 20 may be a different type of sensor, such as a temperature sensor.

As indicated above, pressure sensor 20 may include an optical pressure sensor. In at least some of these embodiments, an optical fiber or fiber optic cable 24 (e.g., a multimode fiber optic) may be attached to pressure sensor 20 and may extend proximally therefrom. An attachment member 26 may attach optical fiber 24 to shaft 12. Attachment member 26 may be circumferentially disposed about and attached to optical fiber 24 and may be secured to the inner surface of shaft 12 (e.g., distal region 16). In at least some embodiments, attachment member 26 is proximally spaced from pressure sensor 20. Other arrangements are contemplated. Additional features and structural elements of the pressure sensor 20 may be seen in FIGS. 4 through 7, which illustrate features of an optical pressure sensing block that may be used as the pressure sensor 20.

In at least some embodiments, distal region 16 may include a portion with a thinned wall and/or an increased inner diameter that defines a housing region 52. In general, housing region 52 is the portion of distal region 16 that ultimately "houses" the pressure sensor (e.g., pressure sensor 20). By virtue of having a portion of the inner wall of shaft 12 being removed at housing region 52, additional space may be created or otherwise defined that can accommodate sensor 20.

In at least some embodiments, it may be desirable for pressure sensor 20 to have reduced exposure along its side surfaces to fluid pressure (e.g., from the blood). Accordingly, it may be desirable to position pressure sensor 20 along a landing region 50 defined along housing region 52. Landing region 50 may be substantially free of slots 18 so that the side surfaces of pressure sensor 20 have a reduced likelihood of being deformed due to fluid pressures at these locations. Distal of landing region 50, housing region 52 may include slots 18 that provide fluid access to pressure sensor 20.

Moreover, one or more of slots 18 may define a fluid pathway that allows blood (and/or a body fluid) to flow from a position along the exterior or outer surface of guidewire 10 (and/or shaft 12), through slots 18, and into the lumen 22 of shaft 12, where the blood can come into contact with pressure sensor 20. Because of this, no additional side openings/holes (e.g., other than one or more slots 18, a single slot 18 extending through the wall of shaft 12, and/or a dedicated pressure port or opening) may be necessary in shaft 12 for pressure measurement. This may also allow the length of distal portion 16 to be shorter than typical sensor mounts or hypotubes that would need to have a length sufficient for a suitable opening/hole (e.g., a suitable "large" opening/hole) to be formed therein that provides fluid access to sensor 20.

A tip member 30 may be coupled to distal region 16. Tip member 30 may include a shaping member 32 and a spring or coil member 34. A distal tip 36 may be attached to shaping member 32 and/or spring 34. In at least some embodiments, distal tip 36 may take the form of a solder ball tip. Tip member 30 may be joined to distal region 16 of shaft 12 with a bonding member 46 such as a weld.

Shaft 12 may include a hydrophilic coating 19. In some embodiments, hydrophilic coating 19 may extend along substantially the full length of shaft 12. In other embodiments, one or more discrete sections of shaft 12 may include hydrophilic coating 19.

Figure 2:
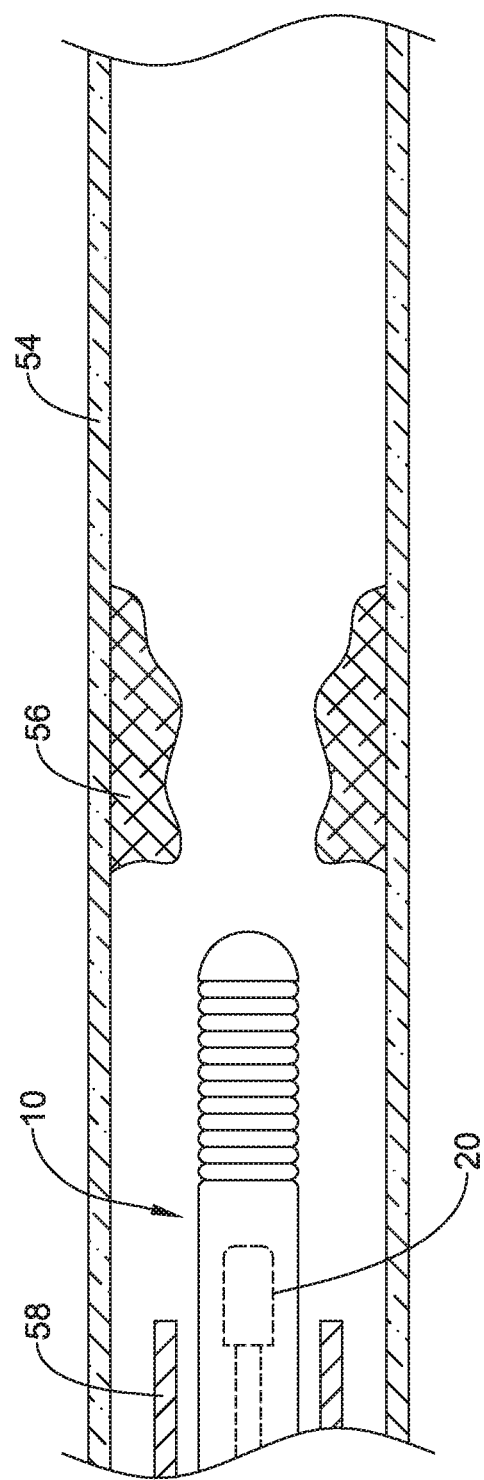
FIG. 2 is a partial cross-sectional view of an example medical device disposed at a first position adjacent to an intravascular occlusion.
Figure 3:
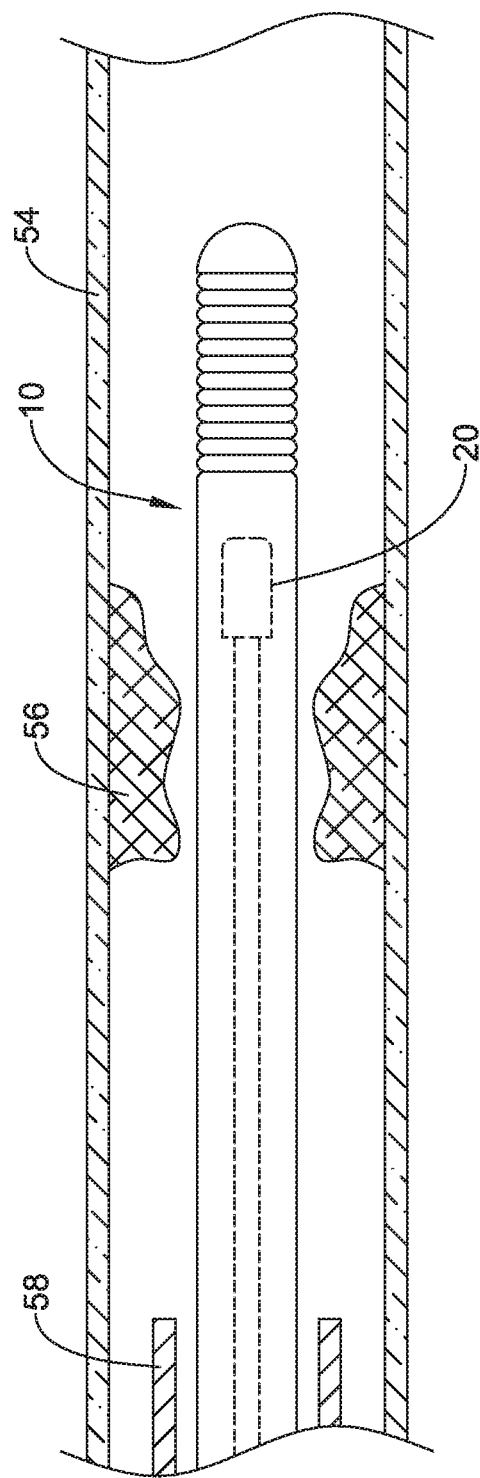
FIG. 3 is a partial cross-sectional view of an example medical device disposed at a second position adjacent to an intravascular occlusion.

In use, a clinician may use guidewire 10 to measure and/or calculate FFR (e.g., the pressure after an intravascular occlusion relative to the pressure before the occlusion and/or the aortic pressure). Measuring and/or calculating FFR may include measuring the aortic pressure in a patient. This may include advancing guidewire 10 through a blood vessel or body lumen 54 to a position that is proximal or upstream of an occlusion 56 as shown in FIG. 2. For example, guidewire 10 may be advanced through a guide catheter 58 to a position where at least a portion of sensor 20 is disposed distal of the distal end of guide catheter 58 and measuring the pressure within body lumen 54. This pressure may be characterized as an initial pressure. In some embodiments, the aortic pressure may also be measured by another device (e.g., a pressure sensing guidewire, catheter, or the like). The initial pressure may be equalized with the aortic pressure. For example, the initial pressure measured by guidewire 10 may be set to be the same as the measured aortic pressure. Guidewire 10 may be further advanced to a position distal or downstream of occlusion 56 as shown in FIG. 3 and the pressure within body lumen 54 may be measured. This pressure may be characterized as the downstream or distal pressure. The distal pressure and the aortic pressure may be used to calculate FFR.

It can be appreciated that an FFR system that utilizes an optical pressure sensor in a pressure sensing guidewire may be navigated through the tortuous anatomy. This may include crossing relatively tight bends in the vasculature. Because of this, and for other reasons, it may be desirable of pressure sensing guidewire to be relatively flexible, for example adjacent to the distal end. It can be appreciated that in relatively flexible guidewires, bending the guidewire could result in contact between an inner surface of the guidewire and, for example, the pressure sensor. Such contact could lead to alterations and/or deformations of the pressure sensor, potentially leading to pressure reading offsets. Accordingly, disclosed herein are pressure-sensing guidewires that may include structural features that may help to reduce contact between the pressure sensor and the inner surface of the guidewire and, therefore, help to reduce the possibility of pressure reading offsets.

Figure 4:
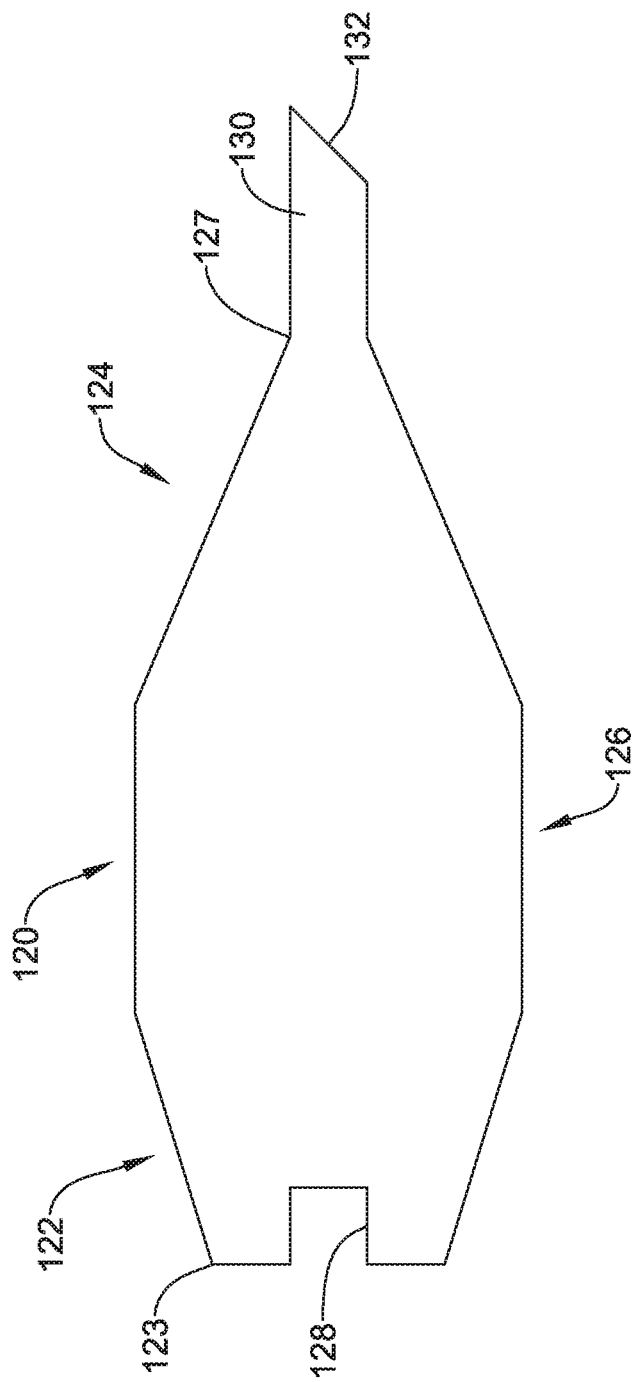
FIGS. 4 through 7 illustrate features of the optical pressure sensing block included as part of the example medical device of claim 1.

FIG. 4 illustrates an optical pressure sensing block 120 that may be used, for example, as the basis for the pressure sensor 20 as shown in FIGS. 1-3. In some embodiments, for example as will be discussed with respect to FIGS. 8-11, a plurality of individual optical pressure sensing blocks 120 may be machined from a block of glass. In some cases, the distal and proximal profiles of a plurality of optical pressure sensing blocks 120 may be milled, etched or otherwise formed in either side of a glass block. The individual optical pressure sensing blocks 120 may then be diced or otherwise cut apart. In some cases, additional elements such as a pressure sensing membrane may be secured to the plurality of optical pressure sensing blocks 120 before they are cut apart. In some instances, the pressure sensing membranes may be added after the optical pressure sensing blocks 120 are cut apart. It will be appreciated that this manufacturing discussion is illustrative only.

In some embodiments, as illustrated, the optical pressure sensing block 120 may be considered as including a distal portion 122 and a proximal portion 124. A center portion 126 is disposed between the distal portion 122 and the proximal portion 124. In some cases, as illustrated, the center portion 126 may have a constant or relatively constant diameter. The distal portion 122 may taper from the center portion 126 towards a distal end 123 of the distal portion 122. In some instances, the proximal portion 124 may taper from the center portion 126 towards a proximal end 127 of the proximal portion 124. While not illustrated, in some cases it is contemplated that a cross-sectional diameter of the optical pressure sensing block 120 may vary smoothly from a maximum somewhere within the center portion 126 towards each of the distal end 123 and the proximal end 127. In some instances, the center portion 126 may be seen as having a larger cross-sectional diameter than either the distal portion 122 or the proximal portion 124. Thus it will be appreciated that the center portion 126 may help to prevent the distal portion 122 of the optical pressure sensing block 120 from contacting other components of the pressure sensing guidewire 10. In some cases, the optical pressure sensing block 120 is formed of a single or monolithic glass block.

In some embodiments, the optical pressure sensing block 120 may be considered as forming a Fabry-Perot optical sensing device that includes a sensor block including a proximal portion, a distal portion and a center portion disposed between the proximal and distal portions, the center portion having an outer diameter that is greater than an outer diameter of the distal portion and greater than an outer diameter of the proximal portion. The distal portion defines a cavity therein, and there may be a pressure sensing layer disposed over the cavity.

Figure 5:
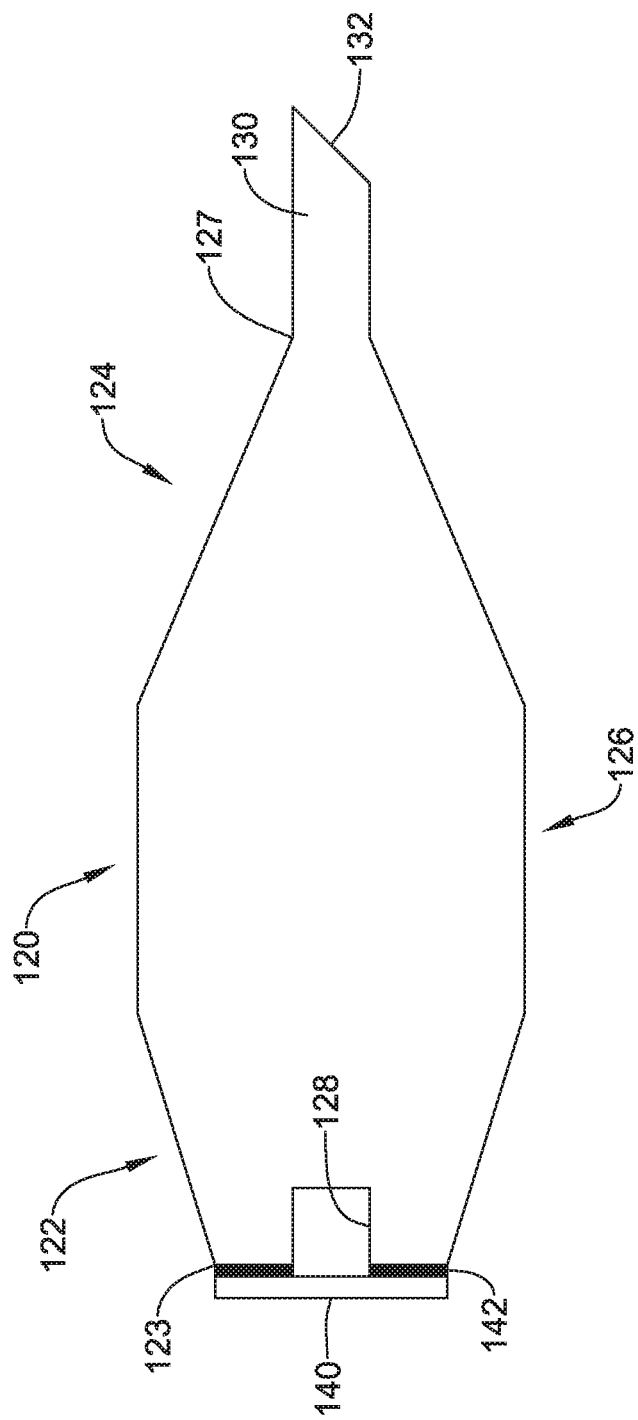

The distal portion 122 of the optical pressure sensing block 120 may include a recess 128 formed in the distal end 123 that helps to form the pressure sensor 20. As is shown in FIG. 5, a pressure sensing membrane may span the recess 128. In some embodiments, as illustrated for example in FIG. 4, the proximal portion 124 of the optical pressure sensing block 120 extends proximally to form an optical fiber connector 130. The optical fiber connector 130 may be integrally formed as part of the optical pressure sensing block 120, and may be configured for attachment to an optical fiber such as the optical fiber 24 shown in FIGS. 1-3. In some cases, the optical fiber connector 130 may be configured to improve the accuracy and effectiveness of a connection between the optical pressure sensing block 120 and the aforementioned optical fiber 24. In some cases, the optical fiber connector 130 may have an angled proximal end 132 that may facilitate fusion splicing between the optical fiber connector 130 and an optical fiber such as the optical fiber 24. In some cases, the proximal end 132 may instead be flat, rather than angled, depending on how the optical fiber is to be attached. It will be appreciated that because the optical fiber 24 is glass, and the optical fiber connector 130, by virtue of being an integral part of the optical pressure sensing block 120, is also glass, an accurate connection can be achieved using fusion splicing. Fusion splicing is a process known for attaching one optical fiber to another optical fiber, for example.

Figure 6:
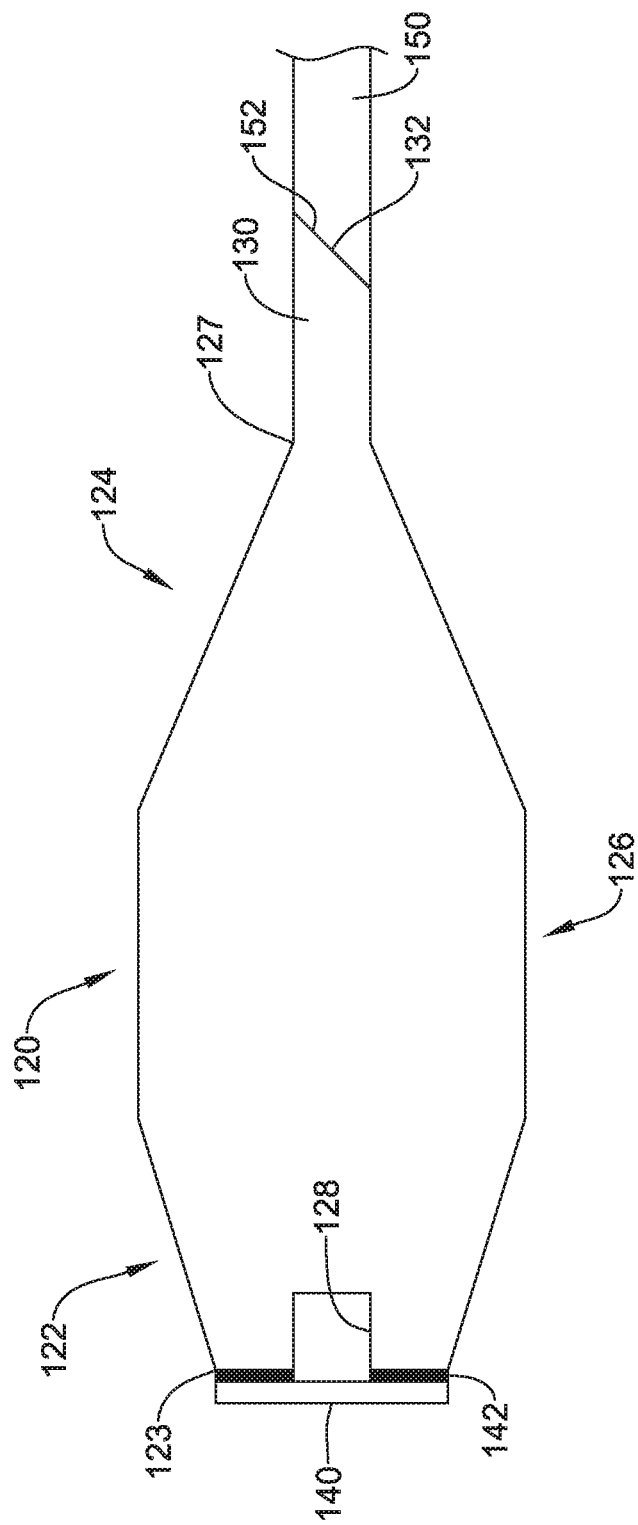

In FIG. 5, it can be seen that a pressure sensing membrane 140 has been secured to the distal end 123 of the optical pressure sensing block 120 via a eutectic bond 142. In some cases, the pressure sensing membrane 140 may be a thin layer of silicon that can flex relative to the void 128 in response to changes in pressure adjacent the pressure sensing membrane 140 opposite the void 128. FIG. 6 illustrates inclusion of an optical fiber 150 that may, for example, represent the optical fiber 24 shown and discussed herein. In the illustrated embodiment, the optical fiber 150 has a distal end 152 that is angled in a complementary fashion to the proximal end 132 of the optical fiber connector 130. It will be appreciated that if the proximal end 132 of the optical fiber 130 is not angled, or has a different profile, that the distal end 152 of the optical fiber 150 will have a corresponding profile.

Figure 7:
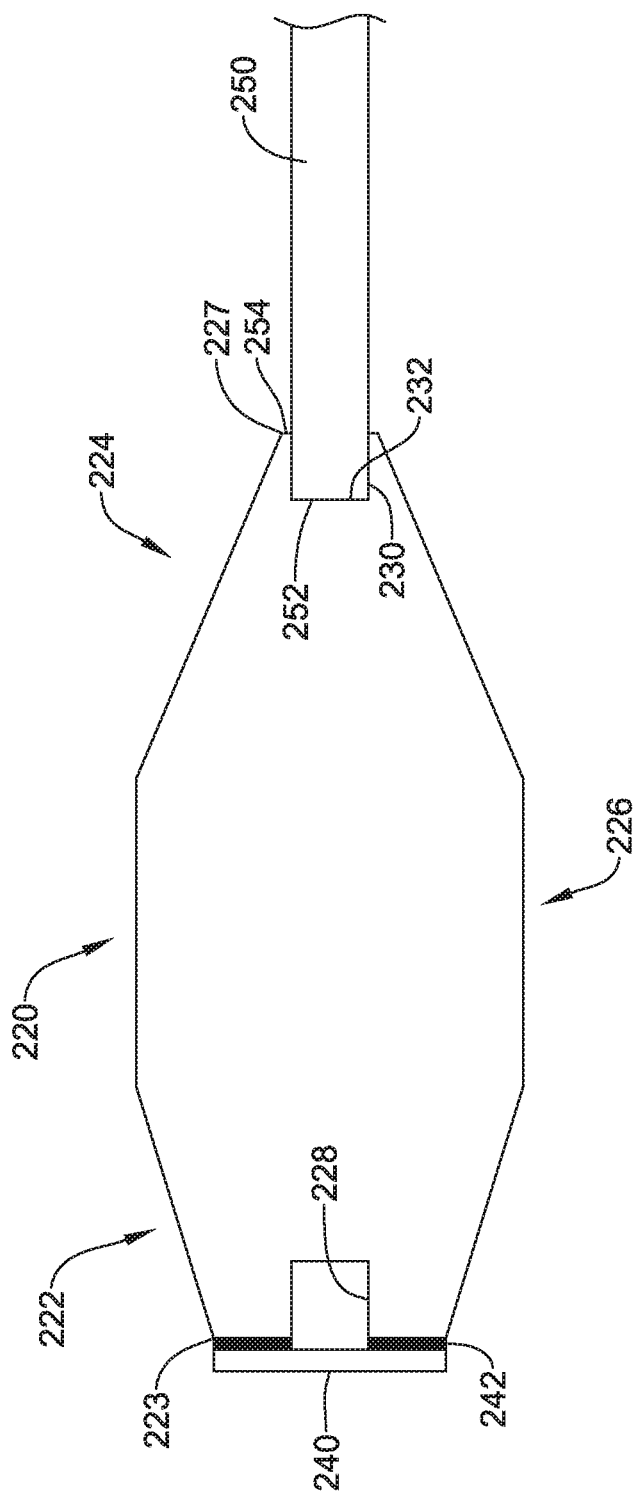

In some cases, as shown in FIG. 7, the optical fiber connector may instead be an aperture drilled or otherwise formed in the optical pressure sensing block 220. It will be appreciated that this may further improve alignment between the optical pressure sensing membrane at the opposing end of the optical pressure sensing block 220. The optical pressure sensing block 220 includes a distal portion 222 and a proximal portion 224. A center portion 226 is disposed between the distal portion 222 and the proximal portion 224. In some cases, as illustrated, the center portion 226 may have a constant or relatively constant diameter. The distal portion 222 may taper from the center portion 226 towards a distal end 223 of the distal portion 222. In some instances, the proximal portion 224 may taper from the center portion 226 towards a proximal end 227 of the proximal portion 224. While not illustrated, in some cases it is contemplated that a cross-sectional diameter of the optical pressure sensing block 220 may vary smoothly from a maximum somewhere within the center portion 226 towards each of the distal end 223 and the proximal end 227.

The distal portion 222 of the optical pressure sensing block 220 may include a recess 228 formed in the distal end 223 that helps to form the pressure sensor 20. A pressure sensing membrane 240 has been secured to the distal end 223 of the optical pressure sensing block 220 via a eutectic bond 242. In some cases, the pressure sensing membrane 240 may be a thin layer of silicon that can flex relative to the void 228 in response to changes in pressure adjacent the pressure sensing membrane 240 opposite the void 228.

In this illustration, an optical fiber connector 230 is an aperture that is formed within the proximal end 227 of the proximal portion 224. The aperture forming the optical fiber connector 230 has a diameter that is about the same as a diameter of an optical fiber 250 such the optical fiber 250 may be inserted into the optical fiber connector 230 but is located by the optical fiber connector 230 such that there is no play, or relative movement between the optical fiber connector 230 and the optical fiber 250. In some cases, the optical fiber connector 230 has a bottom surface 232 that is complementary to a profile of a distal end 252 of the optical fiber 250. Once the optical fiber 250 is firmly secured within the optical fiber connector 230, the optical fiber 250 may be secured in place by an adhesive 254 placed about the optical fiber 250 near the proximal end 227 of the proximal portion 224.

Figure 8:
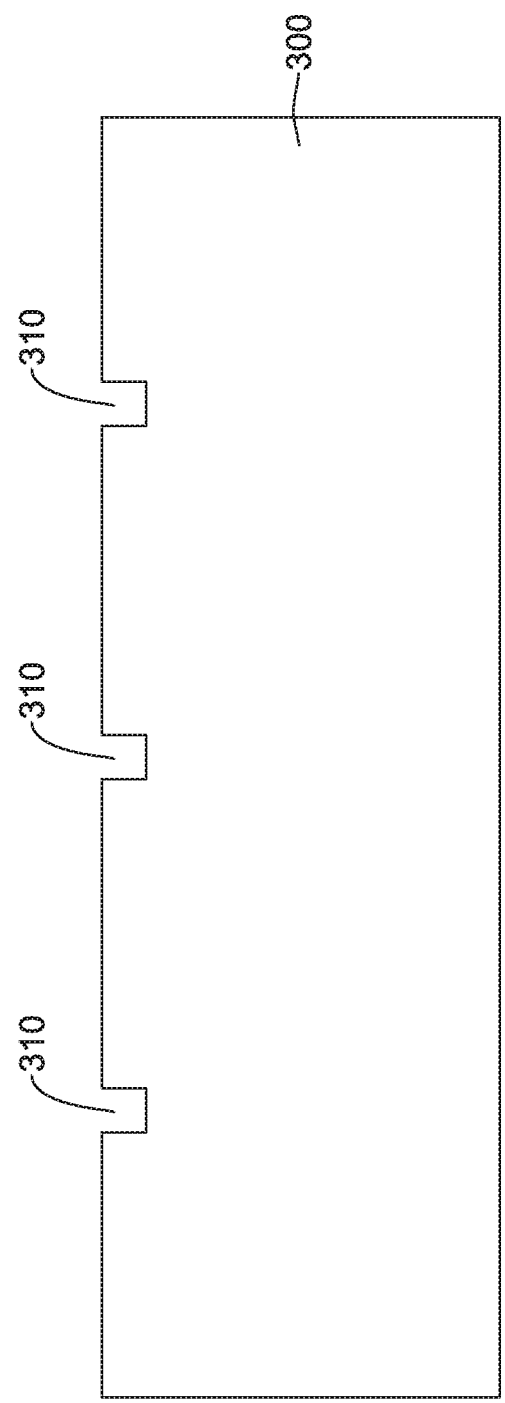
Figure 9:
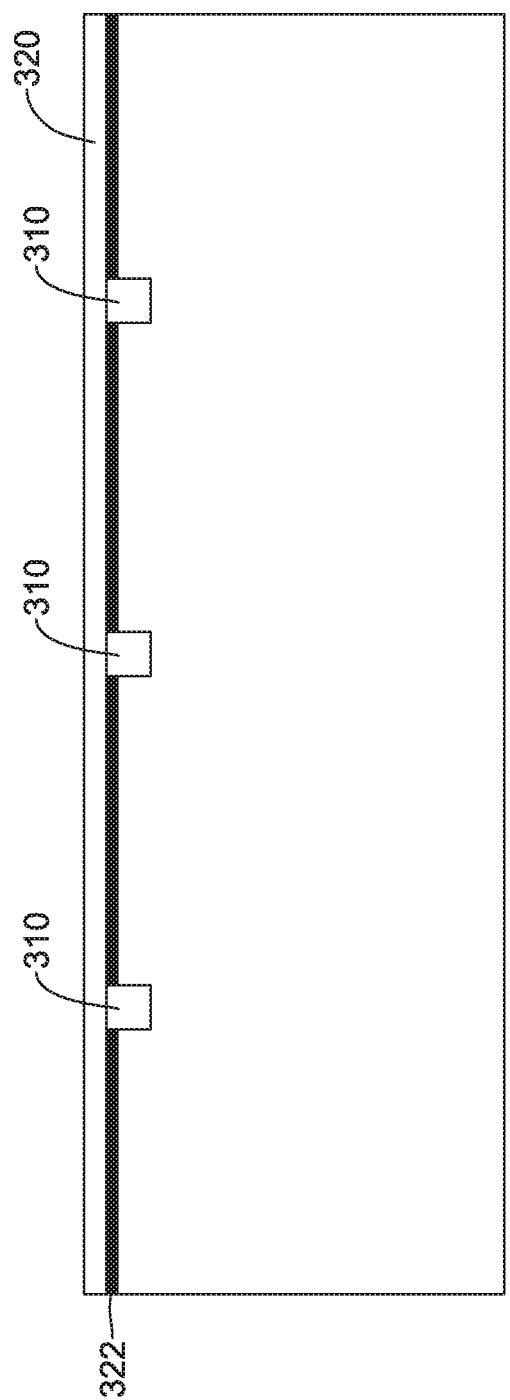
Figure 10:
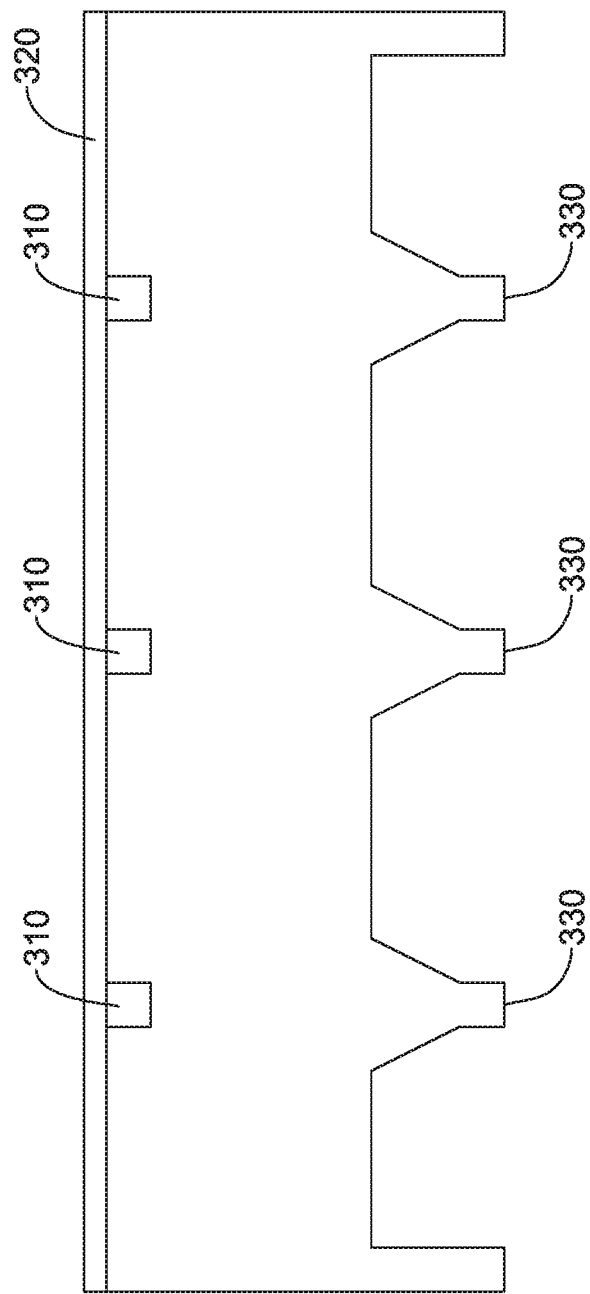

FIGS. 8 through 11 provide an illustrative but non-limiting manufacturing method for the optical pressure sensing block 120. As shown in FIG. 8, pockets 310 may be milled into a glass wafer 300. A silicon membrane wafer 320 may be disposed over the glass wafer 300 and heat and pressure may be applied to create a eutectic bond 322 between the silicone membrane wafer 320 and the glass wafer 300, as shown in FIG. 9. Next, the proximal profile may be machined as shown in FIG. 10, removing material to form optical fiber connectors 330. In some cases, a femtosecond laser system may be used to mill the illustrated profile into the glass wafer 300. Finally, as shown in FIG. 11, the assembly may be diced to form individual optical pressure sensing blocks 340. In some cases, it will be appreciated that the milling shown in FIG. 10 may occur before or after the silicone membrane wafer 320 is attached to the glass block 300 via the eutectic bond 322.

The materials that can be used for the various components of guidewire 10 (and/or other guidewires disclosed herein) and the various tubular members disclosed herein may include those commonly associated with medical devices. For simplicity purposes, the following discussion makes reference to shaft 12 and other components of guidewire 10. However, this is not intended to limit the devices and methods described herein, as the discussion may be applied to other tubular members and/or components of tubular members or devices disclosed herein.

Shaft 12 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of shaft 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of Magnetic Resonance Imaging (MRI) compatibility is imparted into guidewire 10. For example, shaft 12 or portions thereof may be made of a material that does not substantially distort the image and create substantial artifacts (i.e., gaps in the image). Certain ferromagnetic materials, for example, may not be suitable because they may create artifacts in an MRI image. Shaft 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of shaft 12 that may define a generally smooth outer surface for guidewire 10. In other embodiments, however, such a sheath or covering may be absent from a portion of all of guidewire 10, such that shaft 12 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly praraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the guidewire 10 (including, for example, the exterior surface of shaft 12) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of shaft 12, or other portions of guidewire 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

Various embodiments of arrangements and configurations of slots are also contemplated that may be used in addition to what is described above or may be used in alternate embodiments. For simplicity purposes, the following disclosure makes reference to guidewire 10, slots 18, and shaft 12. However, it can be appreciated that these variations may also be utilized for other slots and/or tubular members. In some embodiments, at least some, if not all of slots 18 are disposed at the same or a similar angle with respect to the longitudinal axis of shaft 12. As shown, slots 18 can be disposed at an angle that is perpendicular, or substantially perpendicular, and/or can be characterized as being disposed in a plane that is normal to the longitudinal axis of shaft 12. However, in other embodiments, slots 18 can be disposed at an angle that is not perpendicular, and/or can be characterized as being disposed in a plane that is not normal to the longitudinal axis of shaft 12. Additionally, a group of one or more slots 18 may be disposed at different angles relative to another group of one or more slots 18. The distribution and/or configuration of slots 18 can also include, to the extent applicable, any of those disclosed in U.S. Pat. Publication No. US 2004/0181174, the entire disclosure of which is herein incorporated by reference.

Slots 18 may be provided to enhance the flexibility of shaft 12 while still allowing for suitable torque transmission characteristics. Slots 18 may be formed such that one or more rings and/or tube segments interconnected by one or more segments and/or beams that are formed in shaft 12, and such tube segments and beams may include portions of shaft 12 that remain after slots 18 are formed in the body of shaft 12. Such an interconnected structure may act to maintain a relatively high degree of torsional stiffness, while maintaining a desired level of lateral flexibility. In some embodiments, some adjacent slots 18 can be formed such that they include portions that overlap with each other about the circumference of shaft 12. In other embodiments, some adjacent slots 18 can be disposed such that they do not necessarily overlap with each other, but are disposed in a pattern that provides the desired degree of lateral flexibility.

Additionally, slots 18 can be arranged along the length of, or about the circumference of, shaft 12 to achieve desired properties. For example, adjacent slots 18, or groups of slots 18, can be arranged in a symmetrical pattern, such as being disposed essentially equally on opposite sides about the circumference of shaft 12, or can be rotated by an angle relative to each other about the axis of shaft 12. Additionally, adjacent slots 18, or groups of slots 18, may be equally spaced along the length of shaft 12, or can be arranged in an increasing or decreasing density pattern, or can be arranged in a non-symmetric or irregular pattern. Other characteristics, such as slot size, slot shape, and/or slot angle with respect to the longitudinal axis of shaft 12, can also be varied along the length of shaft 12 in order to vary the flexibility or other properties. In other embodiments, moreover, it is contemplated that the portions of the tubular member, such as a proximal section, or a distal section, or the entire shaft 12, may not include any such slots 18.

As suggested herein, slots 18 may be formed in groups of two, three, four, five, or more slots 18, which may be located at substantially the same location along the axis of shaft 12. Alternatively, a single slot 18 may be disposed at some or all of these locations. Within the groups of slots 18, there may be included slots 18 that are equal in size (i.e., span the same circumferential distance around shaft 12). In some of these as well as other embodiments, at least some slots 18 in a group are unequal in size (i.e., span a different circumferential distance around shaft 12). Longitudinally adjacent groups of slots 18 may have the same or different configurations. For example, some embodiments of shaft 12 include slots 18 that are equal in size in a first group and then unequally sized in an adjacent group. It can be appreciated that in groups that have two slots 18 that are equal in size and are symmetrically disposed around the tube circumference, the centroid of the pair of beams (i.e., the portion of shaft 12 remaining after slots 18 are formed therein) is coincident with the central axis of shaft 12. Conversely, in groups that have two slots 18 that are unequal in size and whose centroids are directly opposed on the tube circumference, the centroid of the pair of beams can be offset from the central axis of shaft 12. Some embodiments of shaft 12 include only slot groups with centroids that are coincident with the central axis of the shaft 12, only slot groups with centroids that are offset from the central axis of shaft 12, or slot groups with centroids that are coincident with the central axis of shaft 12 in a first group and offset from the central axis of shaft 12 in another group. The amount of offset may vary depending on the depth (or length) of slots 18 and can include other suitable distances.

Slots 18 can be formed by methods such as micromachining, saw-cutting (e.g., using a diamond grit embedded semiconductor dicing blade), electron discharge machining, grinding, milling, casting, molding, chemically etching or treating, or other known methods, and the like. In some such embodiments, the structure of the shaft 12 is formed by cutting and/or removing portions of the tube to form slots 18. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 110 may include forming slots 18 shaft 12 using these or other manufacturing steps.

In at least some embodiments, slots 18 may be formed in tubular member using a laser cutting process. The laser cutting process may include a suitable laser and/or laser cutting apparatus. For example, the laser cutting process may utilize a fiber laser. Utilizing processes like laser cutting may be desirable for a number of reasons. For example, laser cutting processes may allow shaft 12 to be cut into a number of different cutting patterns in a precisely controlled manner. This may include variations in the slot width, ring width, beam height and/or width, etc. Furthermore, changes to the cutting pattern can be made without the need to replace the cutting instrument (e.g., blade). This may also allow smaller tubes (e.g., having a smaller outer diameter) to be used to form shaft 12 without being limited by a minimum cutting blade size. Consequently, shaft 12 may be fabricated for use in neurological devices or other devices where a relatively small size may be desired.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device for measuring blood pressure, comprising:
   an elongated shaft having a proximal region and a distal region and a lumen extending therethrough;
   an optical pressure sensing block disposed within the lumen, the optical pressure sensing block including a central portion, a tapered distal portion having an outer surface that tapers distally from the central portion and a proximal portion that tapers proximally from the central portion, the optical pressure sensing block formed of glass;

a pressure sensing membrane disposed on a distal end of the optical pressure sensing block, the central portion and tapered distal portion in combination keeping the pressure sensing membrane from contacting a side wall of the lumen;

an optical fiber connector extending proximally from the proximal portion; and an optical fiber extending through the lumen and coupled to the optical fiber connector.

2. The medical device of claim 1, wherein the optical fiber connector has a circular cross-sectional shape and has a diameter that is about the same as a diameter of the optical fiber.

3. The medical device of claim 1, wherein the optical fiber is fusion spliced to the optical fiber connector.

4. The medical device of claim 1, wherein the lumen includes an enlarged inner diameter portion within the distal region of the shaft, and the optical pressure sensing block is disposed within the enlarged inner diameter portion.

5. The medical device of claim 1, wherein the sensing membrane is eutectically bonded to the optical pressure sensing block.

6. The medical device of claim 1, wherein the elongated shaft comprises a tubular member having one or more slots formed therein.

7. The medical device of claim 1, further comprising a tip member extending distally from the elongated shaft.

8. The medical device of claim 7, wherein the tip member comprises a shaping member and/or a coil member.

9. A pressure sensing guidewire, comprising:

an elongated tubular member having a proximal region and a distal region and a lumen extending therethrough;

an optical pressure sensing block disposed within the lumen, the optical pressure sensing block formed from a monolithic glass block and including a distal portion, a proximal portion and a central portion disposed between the distal portion and the proximal portion;

a pressure sensing membrane disposed on the distal portion of the optical pressure sensing block; the proximal portion forming an optical fiber connector; and an optical fiber extending through the lumen and including a distal end, the distal end coupled to the optical fiber connector;

wherein an outer surface of the distal portion tapers from the central portion to a position proximate the pressure sensing membrane and the proximal portion tapers from the central portion to the optical fiber connector such that the central portion spaces the pressure sensing membrane away from a side wall of the lumen.

10. The pressure sensing guidewire of claim 9, wherein the optical fiber connector extends proximally from the proximal portion of the optical pressure sensing block and is configured to be fusion spliced to the distal end of the optical fiber.

11. The pressure sensing guidewire of claim 9, wherein the optical fiber connector comprises a recess formed in the proximal portion of the optical pressure sensing block and configured to accommodate the distal end of the optical fiber therein.

12. The pressure sensing guidewire of claim 9, wherein the lumen includes an enlarged inner diameter portion within the distal region of the elongated tubular member, and the optical pressure sensing block is disposed within the enlarged inner diameter portion.

13. The pressure sensing guidewire of claim 9, further comprising a tip member extending distally from the elongated shaft.

14. The pressure sensing guidewire of claim 13, wherein the tip member comprises a shaping member and/or a coil member.

15. A pressure sensing guidewire for measuring fractional flow reserve, the guidewire comprising:

an elongate shaft having a proximal region and a distal region and defining a lumen extending therethrough;

wherein the distal region has a plurality of slots formed therein;

an optical fiber extending within the shaft and including a distal end;

an optical pressure sensing block disposed within the lumen, the optical pressure sensing block including a distal portion, a proximal portion, and a center portion disposed between the distal portion and the proximal portion;

a pressure sensing membrane disposed on a distal end of the optical pressure sensing block;

the proximal portion forming an optical fiber connector extending proximally from the proximal portion and fusion spliced to the distal end of the optical fiber;

an outer surface of the distal portion tapering from the center portion to a position proximate the pressure sensing membrane; and the proximal portion tapering from the center portion to the optical fiber connector.

16. The guidewire of claim 15, wherein the optical pressure sensing block comprises glass.

17. The guidewire of claim 15, further comprising a recess formed in the distal portion of the optical pressure sensing block beneath the pressure sensing membrane.

18. The guidewire of claim 15, wherein the optical fiber connector is configured to improve the accuracy of a connection between the distal end of the optical fiber and the optical fiber connector.

* * * * *